US011426241B2

(12) United States Patent
Jeszenszky et al.

(10) Patent No.: US 11,426,241 B2
(45) Date of Patent: Aug. 30, 2022

(54) DEVICE FOR INTRAOPERATIVE IMAGE-CONTROLLED NAVIGATION DURING SURGICAL PROCEDURES IN THE REGION OF THE SPINAL COLUMN AND IN THE ADJACENT REGIONS OF THE THORAX, PELVIS OR HEAD

(71) Applicant: SpineMind AG, Stans (CH)

(72) Inventors: Dezsö János Jeszenszky, Kuesnacht (CH); Tamás Fülöp Fekete, Zurich (CH)

(73) Assignee: SpineMind AG, Stans (CH)

( * ) Notice: Subject to any disclaimer, the term of this patent is extended or adjusted under 35 U.S.C. 154(b) by 858 days.

(21) Appl. No.: 16/064,499

(22) PCT Filed: Dec. 15, 2016

(86) PCT No.: PCT/CH2016/000155
§ 371 (c)(1),
(2) Date: Jul. 16, 2018

(87) PCT Pub. No.: WO2017/106980
PCT Pub. Date: Jun. 29, 2017

(65) Prior Publication Data
US 2018/0368921 A1 Dec. 27, 2018

(30) Foreign Application Priority Data
Dec. 22, 2015 (EP) .................... 15405076

(51) Int. Cl.
*A61B 34/10* (2016.01)
*A61B 34/20* (2016.01)
(Continued)

(52) U.S. Cl.
CPC ............ *A61B 34/20* (2016.02); *A61B 5/0507* (2013.01); *A61B 6/5247* (2013.01);
(Continued)

(58) Field of Classification Search
CPC ......... A61B 34/10; A61B 34/20; A61B 34/25; A61B 2034/0251; A61B 2034/2055;
(Continued)

(56) References Cited

U.S. PATENT DOCUMENTS 5,224,376 A * 7/1993 Elings .................... B82Y 35/00
73/105
5,910,827 A * 6/1999 Kwan .................. H04N 19/895
375/240.27
(Continued)

FOREIGN PATENT DOCUMENTS

CN 103118601 A 5/2013
DE 100 15 826 A1 10/2001
(Continued)

OTHER PUBLICATIONS

Lindseth, Ultrasound Guided Surgery: Multimodal Visualization and Navigation Accuracy. Norwegian University of Science and Technology. 2002. (Year: 2002).*
(Continued)

*Primary Examiner* — Colin T. Sakamoto
(74) *Attorney, Agent, or Firm* — Collard & Roe, P.C.

(57) ABSTRACT

A device for intraoperative, image-controlled navigation during surgical procedures in the spinal and/or adjacent thorax, pelvis or head regions, includes multiple non-x-ray detection devices to be distributed about at least one object to be operated on, and to intraoperatively capture real time image and position data, respectively including information relating to the outer contour of at least one subregion of the object, and to the subregion position relative to the respective detection device. Also, a position determining device for determining respective detection device position relative to a stationary reference system, and a data processing device operatively connected with the detection devices and the position determining device are designed to create, based on
(Continued)

Figure 1:
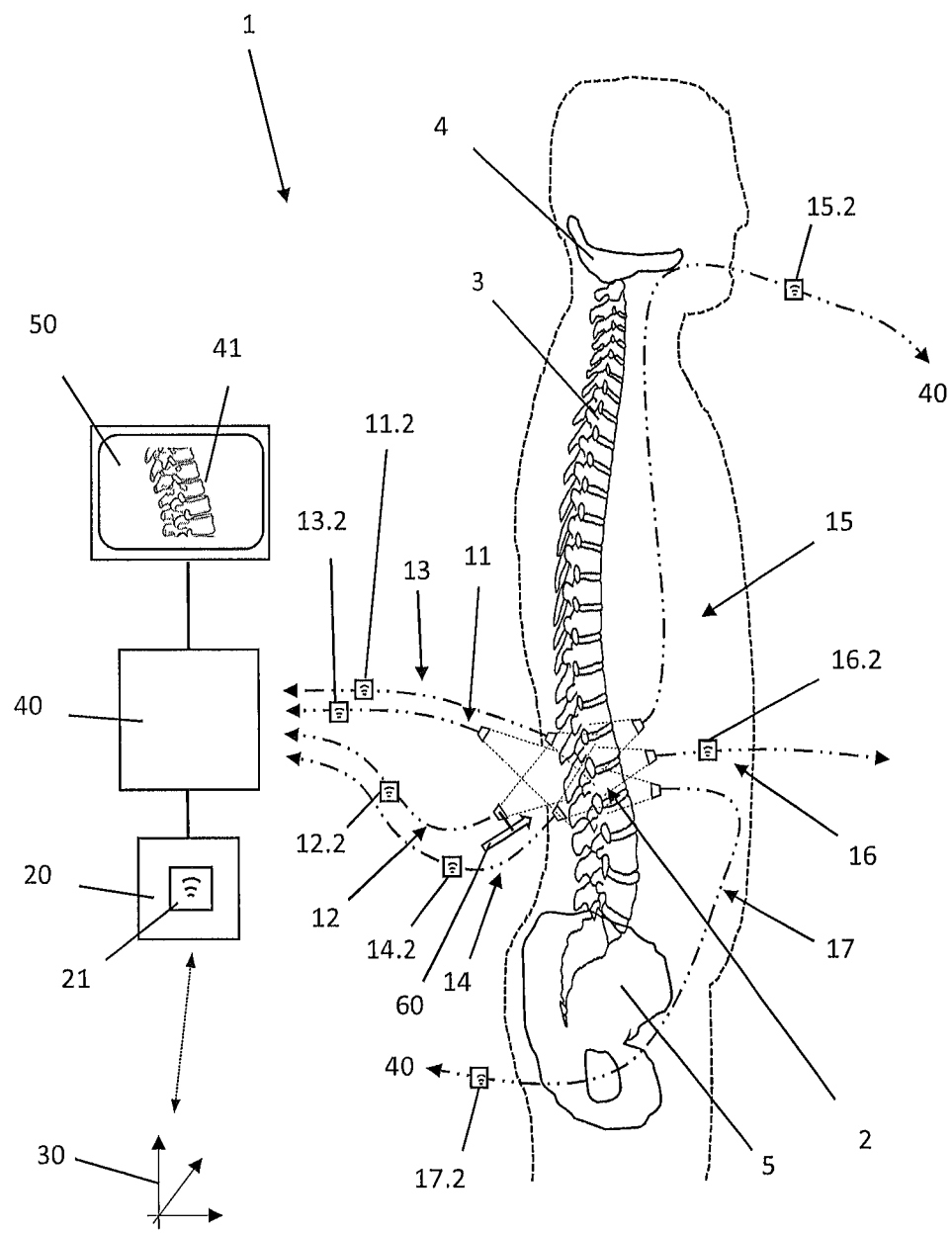

the respective detection device image and position data and the position determining device position data, a virtual real-time image, referenced with respect to the reference system, of the object, and displayed on an image display device.

14 Claims, 3 Drawing Sheets

(51) Int. Cl.
| | |
|---|---|
| *A61B 5/0507* | (2021.01) |
| *A61B 5/06* | (2006.01) |
| *A61B 6/12* | (2006.01) |
| *A61B 8/08* | (2006.01) |
| *A61B 8/12* | (2006.01) |
| *A61B 90/00* | (2016.01) |
| *A61B 6/00* | (2006.01) |
| *A61B 34/00* | (2016.01) |
| *A61B 17/17* | (2006.01) |

(52) U.S. Cl.
CPC .............. *A61B 8/0875* (2013.01); *A61B 8/12* (2013.01); *A61B 8/5253* (2013.01); *A61B 8/5261* (2013.01); *A61B 34/10* (2016.02); *A61B 34/25* (2016.02); *A61B 90/36* (2016.02); *A61B 90/39* (2016.02); *A61B 5/061* (2013.01); *A61B 17/1757* (2013.01); *A61B 2034/107* (2016.02); *A61B 2034/2051* (2016.02); *A61B 2034/2055* (2016.02); *A61B 2034/2072* (2016.02); *A61B 2090/364* (2016.02); *A61B 2090/365* (2016.02); *A61B 2090/371* (2016.02); *A61B 2090/373* (2016.02); *A61B 2090/3782* (2016.02); *A61B 2090/3983* (2016.02)

(58) Field of Classification Search
CPC ............ A61B 5/0507; A61B 5/06–068; A61B 5/0035; A61B 8/0875; A61B 8/12; A61B 8/4245–4263; A61B 8/5253; A61B 8/5261

See application file for complete search history.

(56) References Cited

U.S. PATENT DOCUMENTS

| | | | |
|---|---|---|---|
| 6,768,496 B2 | 7/2004 | Bieger et al. | |
| 9,792,721 B2 | 10/2017 | Kosmecki et al. | |
| 2002/0018588 A1* | 2/2002 | Kusch | A61B 6/583 |
| | | | 382/131 |
| 2005/0157168 A1* | 7/2005 | Kaneko | A61B 1/00009 |
| | | | 348/72 |
| 2008/0232478 A1* | 9/2008 | Teng | H04N 19/174 |
| | | | 375/240.27 |
| 2009/0318756 A1 | 12/2009 | Fisher et al. | |
| 2011/0184684 A1* | 7/2011 | Li | A61B 90/36 |
| | | | 702/94 |
| 2014/0218366 A1* | 8/2014 | Kosmecki | G06T 15/08 |
| | | | 345/426 |
| 2014/0239949 A1* | 8/2014 | Huang | G01R 33/543 |
| | | | 324/307 |
| 2015/0138223 A1* | 5/2015 | Sorkine Hornung | H04N 1/6077 |
| | | | 345/591 |
| 2015/0359512 A1* | 12/2015 | Boctor | A61B 8/469 |
| | | | 600/444 |

FOREIGN PATENT DOCUMENTS

| | | |
|---|---|---|
| JP | 2001-204738 A | 7/2001 |
| WO | 96/11624 A2 | 4/1996 |
| WO | 2012/042413 A1 | 4/2012 |
| WO | 2013/001031 A2 | 1/2013 |

OTHER PUBLICATIONS

International Search Report of PCT/CH2016/000155, dated Apr. 18, 2017.

* cited by examiner

DEVICE FOR INTRAOPERATIVE IMAGE-CONTROLLED NAVIGATION DURING SURGICAL PROCEDURES IN THE REGION OF THE SPINAL COLUMN AND IN THE ADJACENT REGIONS OF THE THORAX, PELVIS OR HEAD

CROSS REFERENCE TO RELATED APPLICATIONS

This application is the National Stage of PCT/CH2016/000155 filed on Dec. 15, 2016, which claims priority under 35 U.S.C. § 119 of European Application No. 15405076.9 filed on Dec. 22, 2015, the disclosure of which is incorporated by reference. The international application under PCT article 21(2) was not published in English.

The invention relates to a device for intraoperative image-controlled navigation during surgical procedures.

Various devices and methods are known from the prior art for intraoperative image-controlled navigation, which visualize to the surgeon, during an operation, the arrangement of the instruments or implants used, relative to the patient. The fundamental aim of these navigation devices and methods is to improve the three-dimensional orientation of the surgeon during the operation and thereby, ultimately, to increase the safety of the patient. A multitude of navigation systems are based on the correlation or respectively referencing, designated as registering, of preoperative image data, for example computer tomography (CT) and/or magnetic resonance tomography (MRT) image data, with the intraoperative coordinate system of the patient.

Basically, such registering methods are known from medical image processing. There, they serve to optimally correlate two or more images of the same scene, or at least of similar scenes, in order to obtain better knowledge from their combination. Thus, e.g. MRT images which present soft tissue or brain structures well, are superimposed with CT images, in order for instance to be able to reproduce the three-dimensional relationships between osseous structures (CT images) and neutral elements (MRT images). The images which are to be registered differ generally from one another, for instance because they were taken from different positions, at different times or by different methods (modalities). For registering, generally one of the images is established as reference image, whilst the remaining object images are adapted optimally to the reference image through the calculation of a compensating transformation, for instance on the basis of minimizing of the mean square error.

In an analogous manner, for the registering process during the image-controlled navigation, a transformation is carried out between the coordinate system of the patient and the set of preoperative image data, which is based on the identification of features or respectively markers which can be represented both in the preoperative image data and also in the actual operation situation on the patient. The result of the registering is in most cases an affine transformation, which contains a rotation, translation and scaling of the image data to the patient coordinate system.

For the representation of the patient coordinate system on the one hand so-called anatomical or artificial landmarks, and on the other hand intraoperative imaging methods are used.

The registering by means of anatomical landmarks requires the selection of suitable anatomical points on the patient. In spinal column surgery, the anatomical landmarks are selected such that they lie for instance on the bone surface of the vertebra. In order to scan this, generally the bone surface of the vertebrae is exposed. The selected features should surround the operating field as much as possible, because thereby the accuracy of the registering increases. However, methods based on anatomical landmarks are frequently associated with a great expenditure of time. Thus, indeed, in the presence of a normal anatomy the precise locating of the landmarks is possible relatively accurately. In contrast thereto, the identifying of landmarks is distinctly impeded and less accurate in patients with pathological changes with regard to the spinal column, for instance in the case of tumours, congenital, degenerative or traumatic alterations. This often results in only an unsatisfactory navigation accuracy. In addition, this method is very time-consuming.

A further development presents the use of artificial landmarks and intraoperative imaging methods, which co-reproduce the artificial landmarks. Systems which are based on artificial landmarks generally consist of a location sensor, a computer, a display apparatus and various localizers serving as artificial landmarks. The localizers are suitable reference bodies, the three-dimensional location of which is measured by the location sensor which is used. For navigation, these localizers, e.g. in the form of bone screws, are secured to the patient or to implants. Compared to anatomical landmarks, the positions of artificial landmarks can be measured substantially more exactly in the image data and in reality, i.e. in the actual operation situation on the patient, whereby the accuracy of registering is increased. However, artificial landmarks are also subject to interfering influences. These are primarily intraoperative displacements of the landmarks, caused by intraoperative manipulations on the patient or also by inadvertent displacement during the operation, which again makes very time-consuming multiple registering necessary. With the knowledge that it might possibly only be noticed too late that artificial landmarks have shifted during the operation, ultimately the basic trust in the navigation is reduced.

In contrast, with the use of intraoperative imaging methods the expenditure of time is significantly less and the registering of the patient coordinate system with the image data is essentially more reproducible. Above all, the x-ray based registering or a registering based on 2D- or 3D-image intensifiers or respectively intraoperative CT is very established in this connection. Here, for example, a preoperatively obtained, CT-based two- or three-dimensional image of the spinal column is merged with an intraoperative two-dimensional x-ray image of the spinal column via software algorithms, or a 3D data set is created intraoperatively (intraoperative CT or 3D-image intensifier), whereby it is possible in particular that the operator can follow for instance the position of the operation instruments and the location of introduced implants, for instance screws, intraoperatively in real time at a three-dimensional data set of the spinal column. In addition, the intraoperative imaging by means of x-rays additionally during the operation enables the location of the implanted implants to be monitored and, if applicable, corrected, with this leading, through repeated imaging by means of x-rays, to higher and usually considerable doses of radiation. The assessment and adaptation of the alignments of the spinal column is also possible with intraoperative imaging methods. However, many items of apparatus for intraoperative imaging are frequently very inflexible and occupy a large amount of space, so that they have a very restrictive effect on the immediate operating area around the patient. In addition—as already mentioned previously—in those imaging methods which are based on x-ray radiation, the exposure to radiation for the patient and the medical personnel is added as an additional disadvantage.

As an alternative hereto, in addition navigation methods and navigation devices are known from the prior art, which are based on an intraoperative ultrasound imaging, wherein instead of the intraoperative X-ray based image described above, an intraoperatively obtained ultrasound data set is merged with preoperative image data, in order to preferably obtain in real time a three-dimensional data set of the spinal column. Such a device is known for example from the international patent application WO 96/11624. Here, the ultrasound data sets are taken from outside the body in the direction of the inside of the body, by scanning that part of the back which immediately adjoins the bone region which is to be operated on, from the outside with the ultrasound head, i.e. for example sitting on the skin of the back.

In the conventional x-ray based and also in the ultrasound-based intraoperative imaging, the object which is to be operated on is, however, imaged either only in projection or else only partially, in the form of a contour image of a subregion. These projection images or respectively subregion images are used subsequently as a reference, in order to be superimposed with preoperative image data, on the basis of which then a virtual real time image, referenced to the intraoperative image data, is generated. However, this virtual image does not reproduce in real time the object itself which is to be operated on, but rather only its real time position. The projection images or respectively the subregion contour images, however, because they in fact only reproduce the projection or respectively only a subregion—are intrinsically not suitable for the visual reproduction in real time of the entire object to be operated on or respectively of the current intraoperative situation.

It is therefore an object of the present invention to provide a device for intraoperative image-controlled navigation during surgical procedures in the region of the spinal column and/or in the adjacent regions of the thorax, pelvis or head, which permits a virtual, preferably three-dimensional real time image to be generated of the object to be operated on, which for the purpose of navigation is referenced to a stationary reference system. In addition, the device is not to impede the operator during the operation and is to be non-sensitive with respect to any intraoperative interfering influences, so that a sufficient navigation accuracy is always guaranteed.

This problem is solved by a device for intraoperative, image-controlled navigation according to the invention. Advantageous embodiments of the invention are discussed below.

According to the invention, the device comprises multiple detection devices that are not x-ray based, which are each configured to be arranged such that they are distributed about at least one object to be operated on in the region of the spinal column and/or in the adjacent regions of the thorax, pelvis or head, and to intraoperatively capture image and location data in real time, respectively comprising information relating to at least the outer contour of at least one subregion of the object to be operated on, and relating to the location of the subregion relative to the respective detection device.

In terms of the present invention, the three-dimensional surface of the object to be operated on is understood as outer contour of the bone region to be operated on. The location of the subregion relative to the respective detection device is defined, in terms of the present invention, as the three-dimensional arrangement of the captured three-dimensional surface of the object to be operated on relative to the respective detection device, wherein the arrangement/location on the one hand comprises the distance, and on the other hand the three-dimensional orientation/alignment in relation to the respective detection device. The reference point "detection device" is to be understood such that thereby principally the capturing part of the detection device is meant, i.e. the actual detection means, for instance the sensor system. According to the invention, the detection device therefore determines on the one hand the distance, and on the other hand the orientation/alignment of the three-dimensional surface region, respectively captured by it, of the object to be operated on relative to itself. The corresponding location data therefore comprise data both concerning the distance and also the alignment of the outer contour data.

The object to be operated on can comprise basically, but not exclusively, osseous-, other supporting tissue and/or soft tissues (for instance pathological structures, space-occupying lesions or tumours). In the region of the spinal column, the object to be operated on can comprise in particular bony and/or cartilaginous parts of the spinal column itself, for instance one or more vertebrae, or one or more parts of one or more vertebrae (vertebral body, transverse process, spinous process, vertebral arch, projection for ribs), the sacrum (Os sacrum), the coccyx (Os coccygis), and/or one or more intervertebral discs. The object to be operated on can lie in the region of the cervical spine (Pars cervicalis), thoracic spine (Pars thoracica) and/or lumbar spine (Pars lumbalis). Furthermore, the object to be operated on can comprise one or more ligaments or parts thereof, for instance the anterior longitudinal ligament (Ligamentum longitudinale anterius), the posterior longitudinal ligament (Ligamentum longitidinale posterius), one or more yellow ligaments (Ligamenta flava), one or more intertransverse ligaments (Ligamenta intertransversaria), one or more interspinal ligaments (Ligamenta interspinalia) and/or the supraspinal ligament (Ligamentum supraspinale). The object to be operated on can also lie in the pelvic region adjacent to the spinal column, therefore can concern for instance an adjoining region of the osseous pelvis, in particular the pelvic ring. The object to be operated on can also lie in the thorax region adjacent to the spinal column, in particular can concern one or more projections for ribs onto the vertebra, one or more rib(regions) or even—in the case of massive pathological changes—the sternum. The object to be operated on can also lie in the head region adjacent to the spinal column. There, it can comprise in particular the region of the so-called C0 vertebra, that is, the occipital bone (Os occipitale) or respectively the occiput. The object to be operated on can also comprise other soft tissue, in particular nerval elements or pathological structures, in the region of the spinal column and/or in the region of the thorax, pelvis or head adjacent thereto.

According to the invention, the detection devices are respectively configured to capture image data which respectively comprise information relating to at least the outer contour of the object to be operated on or respectively a subregion thereof. Depending on the type or respectively detection principle of the detection device and according to the composition of the object to be operated on, one or more of these detection devices, that are not x-ray based, can sometimes also be configured to also capture imaging information relating to the inner structure of the object to be operated on, in addition to the outer contour of the object to be operated on. Thus, for instance, detection devices based on ultrasound or terahertz radiation may be able, depending on the structure, composition and tissue/material of the object to be operated on, to provide information, beyond the outer contour with a material-dependent penetration depth or even penetration, relating to the inner structure of the object to be operated on.

The device according to the invention comprises furthermore a position-determining device, which is configured to determine, in real time, data relating to the respective position of the detection devices relative to a stationary reference system, preferably to a stationary reference system relative to the operating room. Here, also, the reference point "detection device" with regard to the relative location to the stationary reference system is to be understood such that thereby principally the capturing part of the detection device is meant, i.e. the actual detection means, for instance the sensor system. By the position determining device, as final link in the chain between the object to be operated on and the stationary reference system, it is guaranteed as a whole that—via the location data of the detection devices relative to the respectively captured subregion and furthermore via the location data of the detection devices relative to the stationary reference system—the captured outer contour data of the three-dimensional surface of each subregion of the object to be operated on can be referenced three-dimensionally to the stationary reference system. Thereby, as a whole, information relating thereto is available as to how the individual captured subregions of the three-dimensional surface of the object to be operated on are oriented relative to the stationary reference system.

According to the invention, in addition a data processing device is in operative connection respectively with the multiple detection devices and with the position determining device. The data processing device is configured to generate a virtual, preferably three-dimensional real time image of the object to be operated on, referenced to the stationary reference system, and namely on the basis of the respective image- and location data of the detection devices and on the basis of the respective position data of the position determining device.

For the representation of the virtual real time image, according to the invention in addition an image display device is provided, which is in operative connection with the processing device.

According to the invention, in addition at least one of the multiple detection devices comprises at least one detection means which is configured to be arranged inside the body, in order to capture image data comprising information relating to at least the outer contour of at least one subregion of the object to be operated on, facing the inside of the body.

"Facing the inside of the body" means here that the corresponding outer contour of the spinal column or of the region of the thorax, pelvis or head adjacent to the spinal column lies intracorporeally during the operation. Therefore, "facing the inside of the body" may comprise not only "medial" or "deep", i.e. towards the centre of the body, in particular a "ventrally" situated subregion, but also pointing laterally, laterally obliquely toward the rear, laterally obliquely toward the front, at the rear obliquely upward, at the rear obliquely downward, at the front obliquely upward, at the front obliquely downward, laterally obliquely upward or laterally obliquely downward. These statements of location and direction refer purely by way of definition to a patient who is standing upright. The corresponding subregion may be exposed during the operation, partly exposed or completely surrounded by tissue.

It was recognized in a manner according to the invention that through the use of multiple detection devices which are distributed around the operation site and in particular at least one of which is arranged inside the body, instead of only a limited partial detail or respectively a projection, a substantially more comprehensive image of the object to be operated on can be generated from various viewing angles, which in particular contains information relating to at least the outer contour of at least one subregion of the object to be operated on, facing the inside of the body. Ideally, even a virtual, preferably three-dimensional real time panoramic image or respectively a complete real time 3D reconstruction of the outer contour of the object to be operated on can be generated, which in a manner according to the invention distinctly improves the navigation accuracy and the sense of security for the operator and ultimately the safety of the patient.

In particular, the virtual real time image generated by the device according to the invention is based on actual real time image data which not only permit the monitoring of the real time position of the operation area relative to the stationary reference system, but also reproduce visually in real time the actual outer contour of the object to be operated on quasi in situ.

In an advantageous manner, therefore, with the device according to the invention—in contrast to methods and devices in which the virtual image of the operation site, apart from the position data, are based exclusively on preoperative data or data taken during the first part of the operation, i.e. during the access phase—intraoperative changes to the outer contour of the object to be operated on and in the environment of the operation site are captured visually in real time. Thus, for instance, removals of bone or of other tissue carried out in the operation region, screws which are introduced, operating instruments which are brought into use, corrections to position/adjustments to the alignments or suchlike are captured visually in situ, whereby furthermore the navigation accuracy and the sense of security for the operator are increased in a manner essential to the invention.

Of course, not only one detection device can be configured to be arranged inside the body or respectively to be arranged intraoperatively, but rather at least two, at least three, at least four, at least five, at least six, at least seven, at least eight, at least nine, at least ten, at least eleven, at least twelve or more; in particular two, three, four, five, six, seven, eight, nine, ten, eleven, twelve of the multiple detection devices.

The number and arrangement of the entirety of the multiple detection devices can be determined by the size and position of the object to be operated on. It is conceivable, for example, that the operation concerns only a small part/portion of the spinal column. For this, a small number of detection devices can already be sufficient, which are arranged in a closely limited region around the operation site. In another case, the operation may concern a substantially larger region, which may extend in particular over the entire length of the spinal column, so that a greater number of detection devices is necessary, which are arranged distributed along the spinal column over the entire length of the operation region.

Likewise, the type of detection device may be different according to the position, in particular depending on the arrangement within or outside the body, for the multiple detection devices. It is conceivable for example that a detection device which is arranged inside the body is a detection device based on ultrasound, whereas a detection device of the same device system, which is arranged outside the body, is an optical contour scanner. Through the use of multiple detection devices of different type, more, and more detailed, information relating to the object to be operated on can be obtained in an advantageous manner.

In addition, it is conceivable that the captured subregions of the object to be operated on, which are associated respectively with different detection devices, partially overlap, i.e. that the detection fields of different detection devices partially overlap.

The generation of the virtual real time image can take place such that the individual image data sets captured by the detection devices, which data sets respectively reproduce at least the outer contour of a subregion of the object to be operated on, are compiled by the data processing device into an overall image at least of the outer contour of the object to be operated on. For this, on the one hand, the data determined by the detection device relating to the location, i.e. orientation and distance, of the corresponding subregion relative to the respective detection device are used, and on the other hand the position data, captured by the position determining device, of the respective detection device relative to the stationary reference system are used, in order, by means of this information, to compile the overall image of the object to be operated on from the sets of image data of the individual subregions. For this, in the detection device a specific image registering-, image generating- and/or image processing software can be used, which reconstructs, from the sets of image data, the associated location- or respectively position data, a virtual image at least of the outer contour of the object to be operated on. For the three-dimensionally exact compiling of the individual sets of image data into an overall image, the data processing device can be configured in particular to identify specific image regions which have anatomically distinctive features of the object to be operated on, for example spinous processes, transverse processes, articular processes, ribs, projections for ribs or other distinctive features in the region of the spinal column, pelvis, thorax or occiput. Vessels can also be used as anatomically distinctive features, which are situated in the region of the object to be operated on, for example the Arteria vertebralis, which runs respectively through the Foramen transversarium. Preferably, the data processing device may be configured to seek identical anatomically distinctive objects in the sets of image data, which originate from different detection devices and, by means of the position and orientation of these anatomically distinctive objects, to allocate the sets of image data of the different detection devices three-dimensionally to one another or respectively to arrange them in the correct manner three-dimensionally with respect to one another.

For the generating of the virtual real time image, in particular basically known methods of image registering can come into use. For example, the registering method can comprise the following steps: In a first step, the so-called feature extraction takes place: From the sets of image data which are to be registered, anatomically distinctive features of the object to be operated on, such as e.g. spinous or transverse processes or suchlike, are detected manually or automatically. In a second step, the so-called feature matching, the correspondence of the extracted feature points is generated. For this, the detection device can for example use a function which indicates a qualitative measure for correlations in the real time image data sets of the different detection devices, which is then to be minimized or maximized in an optimization method. In a third step, the transformation calculation takes place, in which a suitable transformation type, e.g. an affine transformation type, a projective transformation type or suchlike, is selected and the transformation parameters are calculated. Finally, in a fourth step, the actual transformation takes place. For this, the sets of image data are transformed with the transformation calculated in the previous step, wherein sometimes also interpolation techniques can also come into use.

According to a first advantageous aspect of the invention, in addition to the real time image data, image data of the object to be operated on, obtained preoperatively or during the access phase, may be integrated into the generating of the virtual real time image. Therefore, provision can be made in particular that the data processing device is configured to superimpose image data of the object to be operated on, obtained preoperatively or during the access phase, with the image data of the detection devices, in order, on the basis of the image data obtained preoperatively or during the access phase, superimposed with the image data of the detection devices, to generate the virtual real time image of the object to be operated on, referenced to the stationary reference system. Here, also, again basically known image registering methods may come into use. Through the additional integration of image data obtained preoperatively, more, and more detailed, information relating to the object to be operated on can be obtained in an advantageous manner.

Basically, however, it is also conceivable that the virtual real time image—with regard to the graphic reproduction of the object to be operated on—is generated only on the basis of the image data obtained preoperatively, superimposed with the outer contour data, whereas the intraoperatively obtained image data, location data and position data are used only for the real referencing of this virtual real time image to the stationary reference system. In this respect, according to an independent idea of the invention, a further device is proposed for intraoperative, image-controlled navigation during surgical procedures in the region of the spinal column and/or in the adjacent regions of the thorax, pelvis or head, which comprises at least one detection device that is preferably not x-ray based, which is configured to capture intraoperatively in real time image and location data which comprise information relating to at least the outer contour of at least one subregion of the object to be operated on and relating to the location of the subregion relative to the detection device. The device comprises, furthermore, a position determining device, is configured to determine in real time data relating to the position of the at least one detection device relative to a stationary reference system. In addition, the device comprises a data processing device in operative connection with the at least one detection device and with the position determining device, which data processing device is configured to superimpose image data of the object to be operated on, obtained preoperatively or during the access phase, with the image data of the at least one detection device, in order, on the basis of the image data obtained preoperatively or during the access phase, superimposed with the image data of the detection device, to generate the virtual real time image of the object to be operated on, referenced to the stationary reference system. Here, also, again basically known image registering methods can come into use. For the representation of the virtual real time image, furthermore an image display device is provided, in operative connection with the data processing device. In this device also, the at least one detection device comprises at least one detection means which is configured to be arranged inside the body, in order to capture image data which comprise information relating to at least the outer contour of at least one subregion of the object to the operated on, facing the inside of the body. In this respect, the at least one detection device serves principally for monitoring the real time position of the operation region relative to the stationary reference system, by capturing at least one subregion of the object to be operated on facing the inside of the body, and as reference region for the superimposing with the image data obtained preoperatively or during the access phase.

Both the device according to one aspect of the invention and also the device according to another aspect of the invention are therefore based on the same inventive idea, namely that (the) at least one detection device or respectively a detection means is configured to be arranged inside the body, in order to capture image data which comprise information relating to at least the outer contour of at least one subregion of the object to be operated on, facing the inside of the body. In a manner according to the invention, it was recognized that the arrangement of the detection device or respectively of the detection means inside the body makes the entire navigation non-sensitive with respect to intraoperative interfering influences, so that a sufficient navigation accuracy is always guaranteed. Through the arrangement inside the body, in particular and if only very small risk exists that the detection field of the detection device is disturbed by the operator. Conversely, the at least one detection device which is able to be arranged inside the body advantageously also does not impair the accessibility of the operation region for the operator. Furthermore, detection means allow other imaging modalities than for example x-radiation, for instance such as ultrasound for example, to be used inside the body. Ultrasound has great advantages in particular in the region of the cervical spine. Thus, for example with correspondingly adapted apparatus such as e.g. apparatus for transoesophageal echocardiography, the cervical spine can be imaged from the front, whereby important structures can be identified (for instance the Arteria vertebralis or nerve roots). At the same time, the movements of the vertebrae, which owing to the great mobility of the cervical spine are caused by surgical manipulation or other manoeuvres, can be compensated continuously. In addition, detection means inside the body allow other aspects to be represented of the object to be operated on, which are not already visible via the access path to the object which is to be operated on. This leads, furthermore, to an increase in accuracy.

It is likewise of importance that owing to the active determining of position by means of the position determining device, the detection device which is able to be arranged inside the body does not have to be fixed. Rather, it can move freely, so that the navigation is not sensitive with respect to intraoperative interfering influences, for instance manipulation on the patient by the operator, rearrangements, respiratory movements or movements of the gut, etc. This is because the position determining device continually captures, according to the invention, on the one hand the respective location of the detection devices relative to the stationary reference system. On the other hand, the detection devices themselves monitor their position permanently in real time relative to the subregion of the operation site captured by them. Hereby, it is made possible to reference the captured outer contour data and consequently the virtual real time image to the stationary reference system in real time.

According to a further advantageous aspect of the invention, the at least one detection device which is able to be arranged inside the body is an ultrasound-based detection device. Ultrasound-based detection devices are particularly suitable for imaging in real time.

In addition, ultrasound-based detection devices allow the outer contour of the object to be operated on to be captured through soft tissue, therefore for instance through adipose tissue, muscular tissue and/or connective tissue. Therefore, they are suitable in particular for image capture of such subregions of the object to be operated on which are not exposed intraoperatively. Furthermore, ultrasound-based detection devices are sometimes configured to enable a distance- and position measurement between detection device and captured object, and to enable a three-dimensional measuring of the object to be operated on, so that the location of the captured subregion relative to the detection device can be captured very accurately in real time. Ultrasound-based detection devices permit, in addition, Doppler-sonographic measurements of flows of fluid. Thus, e.g. important blood vessels may be identified as danger zones or anatomical landmarks. Also, flows of fluid in the cerebrospinal fluid space may be detected, which indeed are mostly minimal, but nevertheless are of greatest relevance with regard to the operation.

It is also conceivable that the at least one detection device which is able to be arranged inside the body is a detection device based on terahertz radiation. The great refractive index of organic tissue in the terahertz spectrum allows very high-contrast recordings and can supplement conventional recording techniques. The radiation is non-ionising and can be used without risk for medical and biological applications. Terahertz radiation is able in some cases, depending on the material/tissue, to even provide information relating to the inner structure of the object to be operated on. Information relating to the inner structure can assist, for example, to differentiate between healthy cells and tumour cells.

In particular, according to a further aspect of the invention, provision can be made that the at least one detection device which is able to be arranged inside the body is configured to be introduced into the body via a preformed body cavity, in particular the nose, the mouth, the pharynx, the oesophagus, the trachea, the gastrointestinal tract, the urinary bladder, or via a blood vessel. For such applications, in particular endoscopic detection devices for endosonography are suitable, for instance for gastroenterological endosonography. The location/position of the latter detection devices for gastroenterological endosonography can take place either directly via the endoscope or for instance by means of electromagnetic waves (radio) toward the exterior. For determining position, in particular location sensors can come into consideration, which are sometimes able to measure acceleration occurring at the endoscope, in order conclude therefrom the location and position of the detection means.

In addition, provision can be made that the at least one detection device which is able to be arranged inside the body is configured to be introduced operatively into a tissue, for example into paravertebral muscular tissue or muscular tissue of the gluteal muscle, and/or into an adipose tissue, for example the epidural space. For such applications, in addition to the conventional endosonography probes described above, in particular so-called sonographic mini-probe systems are suitable, which can be inserted for instance through a biopsy channel and have a substantially thinner probe than in the case of conventional endosonography.

In an analogous manner to the at least one detection device which is able to be arranged inside the body, at least one of the multiple detection devices can be configured to be arranged outside the body, in order to capture image data which comprise information relating to at least the outer contour of a subregion of the object to be operated on, facing the exterior of the body.

In the same manner, provision can be made in addition that the at least one detection device which is able to be arranged outside the body is an ultrasound-based detection device or a detection device based on terahertz radiation. However, it is also conceivable that the at least one detection device which is able to be arranged outside the body is configured as an optical contour scanner.

As position determining devices, for example electromagnetic, in particular optical position determining devices come into consideration, in which on the detection devices respectively a passive position marker or an active position transmitter is arranged, which is monitored via a remotely arranged position marker recognition device or a remotely arranged receiver device, which receives signals emitted by the position transmitter. Such position determining devices are basically known from the prior art, for example the position determining device by Medtronic, marketed for spinal surgery under the brand name "StealthStation".

In order to also provide the operator intraoperatively—as previously explained—with real time information relating to any operating instruments and their position and orientation relative to the operation site, provision can be made according to a further aspect of the invention that the device comprises on the one hand at least one operating instrument, and that on the other hand the position determining device is configured in addition for determining the location of the at least operating instrument relative to the stationary reference system, and the processing unit is, in addition, configured for superimposing an indicator into the virtual real time image, which indicator represents the at least one operating instrument and its location relative to the stationary reference system.

Moreover, provision can be made in a further advantageous aspect of the invention that at least one of the detection devices is able to be arranged, or respectively is arranged, on an operating instrument. For this, the device according to the invention can comprise in addition an operating instrument which is configured to receive at least one detection device, or respectively on which at least one detection device is arranged.

In order to secure the functionality of the device against any external interfering influences and therefore to constantly maintain the sense of security for the operator, provision can be made according to a further advantageous aspect of the invention that the data processing device is configured, in the case of a temporary failure of the determining of the image data, location data and/or position data of at least one of the detection devices, to generate the subregion of the object to the operated on, captured by this detection device, in the virtual real time image on the basis of the image data captured at an earlier point in time by this detection device with functioning determining of location data and position data, wherein the image data of the corresponding subregion, captured at an earlier point in time, are adapted in real time to the current location of the subregions captured by the remaining detection devices.

In case where only the determining of location data and/or position data for one or more the detection devices fails temporarily, but not the image capture of the detection device(s) concerned, provision can be made according to a further aspect of the invention to generate the subregion of the object to be operated on, captured by this detection device, in the virtual real time image, still on the basis of the currently captured image data, but to adapt the currently captured image data of the corresponding subregion with regard to the location relative to the stationary reference system in real time to the current location of the subregions captured by the remaining detection devices.

In addition, provision can be made that the detection devices are configured to communicate with each other, in particular to exchange information relating to their respective position and/or location, preferably relative to the stationary reference system.

Furthermore, provision can be made that at least one of the multiple detection devices, in particular at least one detection means of at least one of the detection devices, are configured to determine the position and/or location of at least one other detection device or respectively the position and/or location of the respective detection means of the at least one other detection device relative to itself and thereby—via the position determining device—relative to the stationary reference system. Hereby, the navigation accuracy can be furthermore distinctly improved. It is conceivable, for example, that one of the multiple detection devices is an ultrasound detection device, which is configured not only to capture image and location data relating to at least one subregion of the object to be operated on, but rather also to capture at least location and position data, preferably also image data, to at least one other detection device relative to itself.

In order to additionally obtain further information relating to the outer contour and in particular the inner structure of the object to be operated on, provision can be made according to a further aspect of the invention that the device comprises, in addition, at least one x-ray based detection device, which is configured to capture intraoperatively in real time image data which comprise information relating to the outer contour and inner structure of at least one subregion of the object to be operated on, wherein the data processing device is operatively connected to the x-ray based detection device and is configured to superimpose the image data of the x-ray based detection device with the image data of the detection devices that are not x-ray based, in order, on the basis of the image data which are superimposed with one another, to generate the virtual real time image of the object to be operated on, referenced to the stationary reference system, which image comprises information relating to the outer contour and inner structure of the object to be operated on. It is also conceivable that in addition image data obtained preoperatively or during the access phase—as described further above—are superimposed with previously mentioned intraoperative data of the x-ray based detection device and detection devices that are not x-ray based.

According to a further aspect of the invention, provision can also be made that the device comprises, in addition, an x-ray based detection device, which is configured to capture intraoperatively in real time image and location data which comprise information relating to the outer contour and inner structure of at least one subregion of the object to be operated on and relating to the location of the subregion relative to the x-ray based detection device, wherein the position determining device is, in addition, configured to determine in real time data relating to the position of the x-ray based detection device relative to the stationary reference system, and wherein the data processing device is in operative connection with the x-ray based detection device and is configured, on the basis of the respective image- and location data of the detection devices that are not x-ray based, the image- and location data of the x-ray based detection device and the respective position data of the position determining device, to generate a virtual, preferably three-dimensional real time image of the object to be operated on, referenced to the stationary reference system, which image comprises information relating to the outer contour and inner structure of the object to be operated on.

Preferably, the x-ray based detection device is as weakly radiating or respectively low-dosed as possible, in order to keep the exposure to radiation as low as possible for the patient and for the operating personnel.

The image display device provided according to the invention for representing the virtual real time image can embodied for example as a stationary monitor in the operating room. However, it is also conceivable that the image display device is embodied as a portable monitor, which can be arranged in particular on the wrist of the operator or on the head in front of the operator's eyes or on an instrument/implement.

Further details of the invention and in particular an exemplary form of embodiment of the proposed device are explained in the following with the aid of the enclosed drawings.

Figure 2:
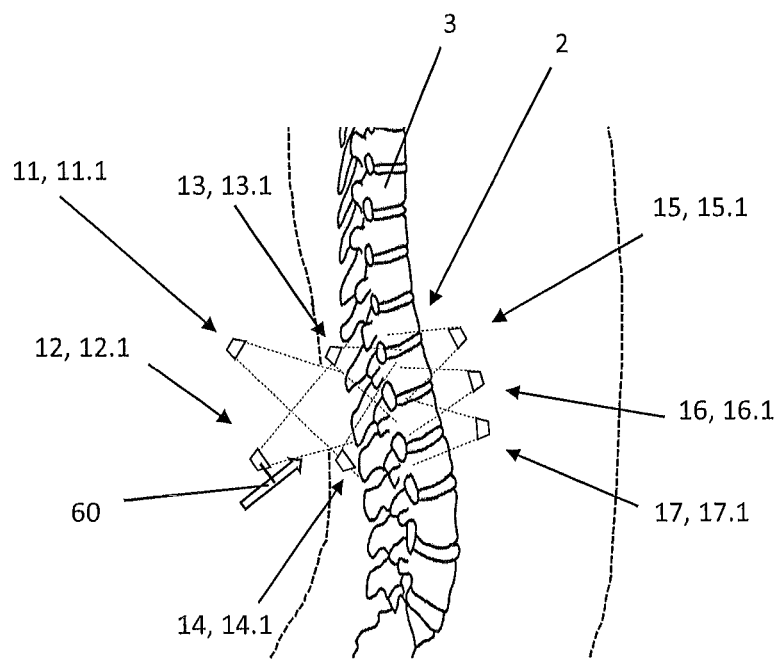
Figure 3:
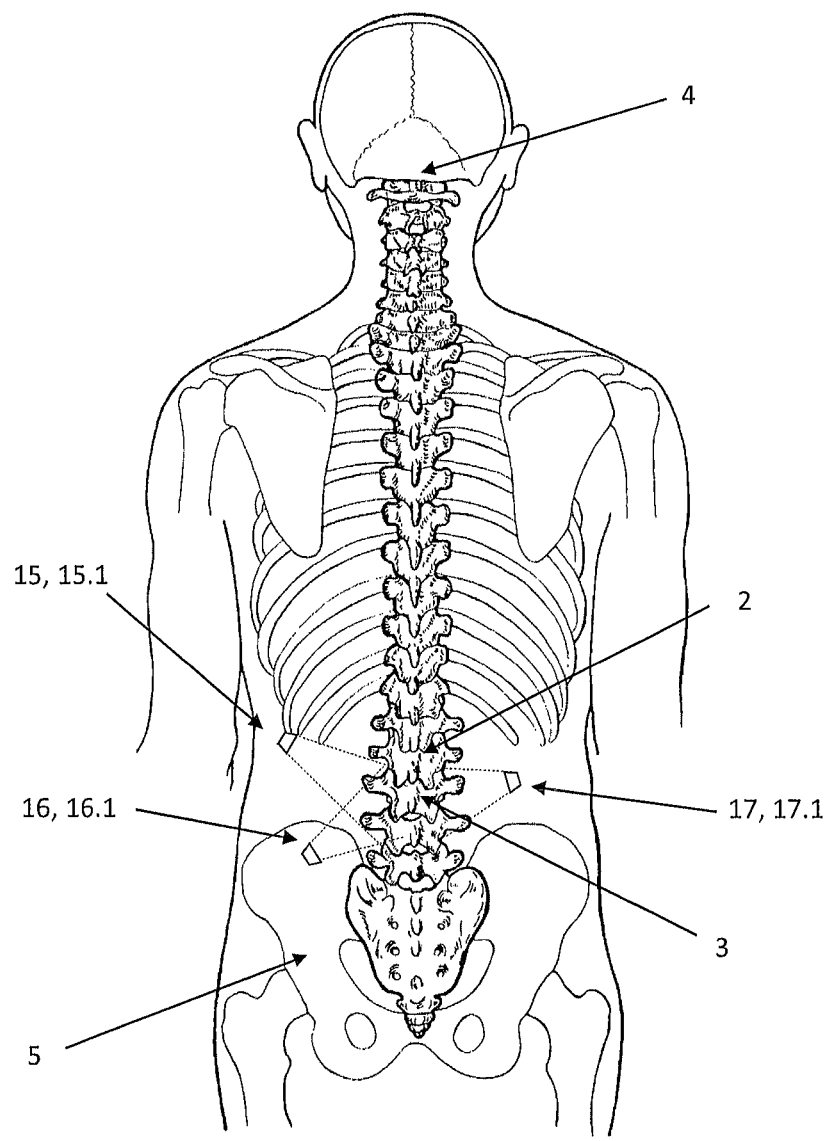

In the drawings, there are shown:

FIG. 1 a schematic view of a possible example embodiment of the device according to the invention, FIG. 2 a detail view of the device according to the invention, in accordance with FIG. 1, and FIG. 3 a schematic view of a further possible arrangement of the device according to the invention.

FIGS. 1 and 2 show a possible example embodiment of the device according to the invention for intraoperative, image-controlled navigation during surgical procedures in the region of the spinal column 3 and/or in the adjacent regions of the thorax, pelvis 5 or head 4.

The device 1 comprises multiple detection devices 11-17 that are not x-ray based, which are each configured to be arranged such that they are distributed about an object 2 to be operated on the spinal column 3 of a patient. Each of these detection devices 11-17 is configured, in addition, to capture in real time intraoperatively respectively at least the outer contour of at least one subregion of the object 2 to be operated on and the location of this subregion relative to the respective detection device 11-17.

As can be seen from FIGS. 1 and 2, the detection devices 11 and 12 or respectively the detection means 11.1 and 12.1 associated therewith are arranged outside the body, whereas the detection devices 13-17 or respectively the detection means 13.1-17.1 associated therewith are arranged inside the body. In the present example embodiment, the detection devices 13 and 14 or respectively the detection means 13.1 and 14.1 associated therewith are introduced operatively into the paravertebral muscular tissue around the exposed bone region 2 which is to be operated on. Likewise, the detection means 16.1 of the detection device 16 is introduced operatively via the abdominal cavity onto the front side of the bone region 2 of the spinal column 3 which is to be operated on.

In contrast, the detection means 15.1 of the detection device 15 is embodied as an endoscope and is introduced via the mouth, the pharyngeal cavity and the oesophagus into the stomach, in order to capture from there the outer contour of a subregion of the bone region 2, to be operated on, from directions of the stomach or of the oesophagus. In a similar manner, the detection means 17.1 of the detection device 17 is also embodied as an endoscope and is introduced rectally into the colon, in order to capture from there the outer contour of another subregion of the bone region 2 to be operated on, from inside the body.

Preferably, in the present example embodiment, all the detection devices 13 to 17 or respectively the detection means 13.1-17.1 associated therewith which are introduced inside the body are embodied as ultrasound-based detection devices or respectively detection means. In the present example embodiment, the two detection means 13.1 and 14.1 are embodied as so-called mini-probe systems, which can be inserted through a respective biopsy channel into the paravertebral muscular tissue. In contrast, the detection means 15.1 and 17.1 are embodied as endoscopic ultrasound probes.

The two detection devices 11 and 12, or respectively the detection means 11.1 and 12.1, arranged outside the body, are embodied in the present example embodiment as optical contour scanners, which respectively scan optically by means of laser light a subregion of the outer contour of the bone region 2 which is to be operated on.

The lines drawn in dashes in FIGS. 1 and 2, which originate from the respective detection means 11.1-17.1, represent respectively the corresponding detection field of the respective detection device 11-17. As can be seen, the detection fields of different detection devices 11-17 can overlap. In the present example embodiment, the detection fields overlap in particular so that an almost complete panoramic representation of the bone region 2 to be operated on is made possible.

All the detection devices 11-17 are, in addition, configured to capture the location of the respectively captured subregion to themselves. In particular, ultrasound-based detection devices and optical contour scanners are suitable for this. This is a basic prerequisite for actually relating the captured outer contour data to a stationary reference system.

In order to determine the respective locations/positions of the detection devices 11-17 with respect to a stationary reference system 30, for instance a stationary reference system 30 with respect to the operating room, the device 1 according to the invention comprises in addition a position determining device 20. The location/position of the detection devices 11-17 means in particular the location/position of the respective detection means 11.1-17.1 with respect to the stationary reference system 30.

In the present example embodiment, the position determining device 20 is embodied as an electromagnetic position recognition system. This system comprises a passive position marker 11.2, 12.2 at each of the detection devices or a position transmitter 13.2-17.2, which is monitored via a remotely arranged combined position marker recognition device and position transmitter-receiver device 21. This combined device is configured to recognize and monitor in real time on the one hand the three-dimensional position of the position markers 11.2 and 12.2 and thereby the three-dimensional position of the detection devices 11 and 12, and on the other hand to receive the position signals emitted from the position transmitters 13.2-17.2 and to determine therefrom a three-dimensional position of the associated detection devices 13-17.

For recognition, the position markers 11.2 and 12.2 must typically be arranged outside the body. In contrast, the position transmitters 13.2-17.2 can be arranged both inside and also outside the body. In the present example embodiment, in particular the position transmitter 16.2 is configured to be arranged inside the body and to transmit, from there outwards, position signals, the information relating to the location of the detection means 16.1, so that they can be received there by the position transmitter-receiver device 21. In the present example embodiment, all the position transmitters 13.2-17.2 are arranged to transmit the respective position signals wirelessly to the position transmitter-receiver device 21. However, it is also conceivable that the transmission of the position signals takes place with one or more of the position transmitters in a wired manner.

The location data of the detection devices 13-17 or respectively of the detection means 13.1-17.1 determined by the position determining device 20 with respect to the stationary reference system 30, and the location data determined by the detection means 13.1-17.1 or respectively the detection devices 13-17 relative to the subregion, captured with regard to outer contour, of the bone region 2 to be operated on, are made available to a data processing device 40.

In addition, the detection devices 13-17 convey to the data processing device 40 respectively image data which represent the corresponding outer contours or respectively outer contour data, captured by them in real time, of the respective subregion of the bone region 2 to be operated on. For the purpose of this data transfer, the detection devices 13-17 and the position determining device 20 are operatively connected with the processing device 40. This data transfer can take place for example via a wired data connection or via a wireless data connection.

Furthermore, the data processing device 40 is configured to generate, on the basis of the transmitted image- and location data, a virtual, preferably three-dimensional real time image 41 of the bone region to be operated on, referenced to the stationary reference system 30, which image is composed from the individual image data sets of the respective subregions. This virtual real time image is based in a manner according to the invention entirely on actual real time image data which permit not only the monitoring of the real time position of the operating region relative to the stationary reference system 30, but also to visually reproduce quasi in situ in real time at least the actual outer contour of the bone region 2 to be operated on. Owing to the multiple detection devices 13-17 arranged inside the body, in a manner according to the invention, a substantially more comprehensive image of the bone region to be operated on can be generated compared to the prior art. Owing to the detection devices 15-17 capturing in the direction of the side of the back, in particular information can be included relating to the outer contour of at least one subregion of the bone region to be operated on, facing the inside of the body. Ideally, even a virtual real time panoramic image of the outer contour of the bone region to be operated on can be generated, whereby the navigation accuracy and the sense of security for the operator is considerably improved.

The virtual real time image 41 generated by the processing device 40 can be represented on an image display device 50 which is in operative connection therewith. In an advantageous manner, this image display device 50 is embodied in the present example embodiment as a portable monitor or respectively as a portable display, which in particular can be fastened to the operator's wrist or in front of the operator's eyes in the manner of monitor eyewear or to an operating implement/instrument.

In the present example embodiment, the device 1 according to the invention comprises in addition at least one operating instrument 60, which—similarly to the detection devices 13-17—is equipped with a position transmitter or with a position marker, by means of which the three-dimensional location of the operating instrument 60 relative to the stationary reference system 30, and thereby to the bone region 2 to be operated on, can be determined. For this purpose, the position determining device 20 is configured in addition for determining the location of the at least one operating instrument relative to the stationary reference system 30. In addition, the processing unit can be configured for superimposing an indicator into the virtual real time image 41, which represents the at least one operating instrument 60 and its location relative to the stationary reference system 30. Hereby, in addition the navigation accuracy and the sense of security for the operator are improved.

As is shown in particular in FIG. 2, provision can be made that at least one of the detection devices—the detection device 12 in the present example embodiment—is arranged on the operating instrument 60. For this, the operating instrument 60 is embodied in particular with a mounting, in order to fasten the detection device 12 thereon.

In order to secure the functionality of the device against any external interfering influences and therefore to constantly maintain the sense of security for the operator, the processing device 40 is configured in addition, in the case of a temporary failure of the image capture and/or of the location/position determining of a detection device 11-17, to generate the subregion of the bone region 2 to be operated on, captured by this detection device 11-17, in the virtual real time image 41 on the basis of the image data captured at an earlier point in time by this detection device 11-17 with functioning determining of location. For this, provision can be made in particular that the image data of the corresponding subregion, captured at an earlier point in time, are adapted in real time to the current location of the subregions captured by the remaining detection devices 11-17.

In case where only the location/position determining for one or more of the detection devices 11-17 fails temporarily, but not the image capture of the concerned detection device(s) 11-17 themselves, provision can be made, in addition, to generate the subregion of the bone region 2 to be operated on, captured by the respectively concerned detection device 11-17, in the virtual real time image 41 on the basis of the currently captured image data. For this, the currently captured image data of the corresponding subregion are adapted, with regard to their location relative to the stationary reference system 41, in real time to the current location of the subregions captured by the remaining detection devices.

FIG. 3 shows a further possible arrangement of detection devices 15-17 or respectively associated detection means 15.1-17.1 of the device according to the invention inside the body. According to this exemplary configuration, at least the detection means 15.1-17.1 of, by way of example, three detection devices 15-17 are arranged laterally on the left or respective right on the spinal column 3 and are aligned such that they capture the outer contour of those regions of the bone region 2 to be operated on which in distal direction face the left and right side of the body. Of course, the arrangement of the detection devices 15-17 according to FIG. 3 can be supplemented by further detection devices which can be arranged inside or outside the body. In particular, the specific arrangement of the detection devices according to FIG. 3 can also be combined with the arrangement of detection devices according to FIGS. 1 and 2. Ideally, with a corresponding all-round arrangement of detection devices inside and outside the body, even a virtual real time panoramic image of the outer contour of the bone region to be operated on can be generated, whereby the navigation accuracy and the sense of security for the operator is considerably improved.

The invention claimed is:

1. A device for intraoperative, image-controlled navigation during surgical procedures on an object to be operated on, said object to be operated on being located on the spinal column or in a region of the thorax, pelvis or head adjacent to the spinal column, said device comprising:

multiple detection devices that are not x-ray based, which are each configured to be arranged such that they are distributed about the object to be operated on, in the region of the spinal column and/or in the adjacent regions of the thorax, pelvis or head, and to intraoperatively capture image data and location data in real time, respectively comprising information relating to at least the outer contour of at least one subregion of the object to be operated on, and relating to the distance and the three-dimensional orientation of the subregion relative to the respective detection device, a position determining device, which is configured to determine in real time data relating to the respective position of the detection devices relative to a stationary reference system, a data processing device in operative connection with the detection devices and with the position determining device, which data processing device is configured to generate, on the basis of the respective image data and location data of the detection devices and of the respective position data of the position determining device, a virtual real time image of the object to be operated on, referenced to the stationary reference system, an image display device in operative connection with the data processing device, for displaying the virtual real time image, wherein at least two of the multiple detection devices each comprise at least one detection means, which is configured to be arranged inside the body, in order to capture image data which comprise information relating to at least the outer contour of at least one subregion of the object to be operated on, facing the inside of the body, wherein each of the at least two of the multiple detection devices is an ultrasound-based detection device or a detection device based on terahertz radiation, wherein the multiple detection devices are distributed about the object to be operated on in such a manner that different ones of the multiple detection devices are enabled to intraoperatively capture in real time individual sets of image data and location data for the outer contours of a plurality of different subregions of the object to be operated on, each individual set of image data captured by one of the multiple detection devices reproducing the outer contour of one of the different subregions of the object to be operated on, wherein the data processing device is configured to generate the real time image of the object to be operated on as a three-dimensional real time image being composed from the individual sets of image data for the outer contours of the plurality of different subregions of the object to be operated on.

2. The device according to claim 1, wherein the data processing device is configured to superimpose preoperatively obtained image data of the object to be operated on with the image data of the detection devices, in order to generate the virtual real time image of the object to be operated on, referenced to the stationary reference system, on the basis of the preoperatively obtained image data, superimposed with the image data of the detection devices.

3. The device according to claim 1, wherein the at least one detection means, able to be arranged inside the body, of the at least one detection device is configured to be introduced into the body via a preformed body cavity or via a blood vessel.

4. The device according to claim 1, wherein the at least one detection means, able to be arranged inside the body, of the at least one detection device is configured to be introduced operatively into a tissue, for example into paravertebral muscular tissue or muscular tissue of the gluteal muscle, and/or into adipose tissue, for example into the epidural space.

5. The device according to claim 1, wherein at least one of the multiple detection devices and/or at least one detection means of at least one of the multiple detection devices is configured to be arranged outside the body, in order to capture image data which comprise information relating to at least the outer contour of a subregion of the object to be operated on, facing the outside of the body.

6. The device according to claim 5, wherein the at least one detection device, able to be arranged outside the body, and/or the at least one detection means, able to be arranged outside the body, is an ultrasound-based detection device or an optical contour scanner or a detection device based on terahertz radiation.

7. The device according to claim 1, wherein the device comprises at least one operating instrument, wherein the position determining device is, in addition, configured to determine in real time data relating to the position of the at least one operating instrument relative to the stationary reference system, and wherein the data processing unit is, in addition, configured to superimpose an indicator, representing the operating instrument and its location, into the virtual real time image.

8. The device according to claim 7, wherein at least one of the multiple detection devices and/or at least one detection means of at least one of the multiple detection devices is configured to be arranged on the at least one operating instrument.

9. The device according to claim 1, wherein the data processing device is configured to generate the subregion of the object to be operated on, captured by this detection device, in the virtual real time image on the basis of the image data captured at an earlier point in time by this detection device with functioning determining of location data and position data, wherein the image data of the corresponding subregion captured at an earlier point in time are adapted in real time to the current location of the other subregions captured by the remaining detection devices.

10. The device according to claim 1, wherein the processing device is configured to generate the subregion of the object to be operated on, captured by this detection device, in the virtual real time image on the basis of the currently captured image data, wherein the currently captured image data of the corresponding subregion are adapted in real time to the current location of the other subregions captured by the remaining detection devices.

11. The device according to claim 1, wherein the device comprises, in addition, at least one x-ray based detection device, which is configured to intraoperatively capture image data in real time which comprise information relating to the outer contour and an inner structure of at least one subregion of the object to be operated on, wherein the data processing device is in operative connection with the x-ray based detection device and is configured to superimpose the image data of the x-ray based detection device with the image data of the detection devices that are not x-ray based, in order, on the basis of the image data which are superimposed with one another, to generate the virtual real time image of the object to be operated on, referenced to the stationary reference system, which comprises information relating to the outer contour and the inner structure of the object to be operated on.

12. The device according to claim 1, wherein the device comprises in addition at least one x-ray based detection device, which is configured to intraoperatively capture in real time image data and location data which comprise information relating to the outer contour and an inner structure of at least one subregion of the object to be operated on and relating to the location of the subregion relative to the x-ray based detection device, wherein the position determining device is in addition configured to determine in real time data relating to the position of the x-ray based detection device relative to the stationary reference system, and wherein the data processing device is, in addition, in operative connection with the x-ray based detection device and is configured, on the basis of the respective image data and location data of the non-x-ray based detection devices, of the image data and location data of the x-ray based detection device and of the data relating to the respective position of the detection devices relative to the stationary reference system and the data relating to the position of the x-ray based detection device relative to the stationary reference system, to generate a virtual real time image of the object to be operated on, referenced to the stationary reference system, which image comprises information relating to the outer contour and the inner structure of the object to be operated on.

13. The device according to claim 1, wherein the detection devices are configured to communicate with one another.

14. The device according to claim 1, wherein at least one of the multiple detection devices is configured to determine the position and/or location of at least one other detection device or respectively the position and/or location of the respective detection means of the at least one other detection device relative to the at least one of the multiple detection devices.

* * * * *